US006066716A

United States Patent [19]
Wallen et al.

[11] Patent Number: 6,066,716
[45] Date of Patent: *May 23, 2000

[54] PURIFIED HEAT SHOCK PROTEIN COMPLEXES

[75] Inventors: Erik S. Wallen; Jan Roigas; Pope L. Moseley, all of Albuquerque, N.Mex.

[73] Assignee: University of New Mexico, Albuquerque, N.Mex.

[ * ] Notice: This patent is subject to a terminal disclaimer.

[21] Appl. No.: 08/934,139

[22] Filed: Sep. 19, 1997

Related U.S. Application Data

[62] Division of application No. 08/717,239, Sep. 20, 1996, Pat. No. 5,747,332.

[51] Int. Cl.$^7$ .................................................. C07K 17/00
[52] U.S. Cl. .......................... 530/350; 530/412; 530/413; 530/402
[58] Field of Search .................................. 530/350, 412, 530/413, 402

[56] References Cited

U.S. PATENT DOCUMENTS

| | | | |
|---|---|---|---|
| 5,114,852 | 5/1992 | Yabusaki et al. | 435/189 |
| 5,132,407 | 7/1992 | Stuehr et al. | 530/395 |
| 5,268,465 | 12/1993 | Bredt et al. | 435/252.3 |
| 5,541,095 | 7/1996 | Hirschberg et al. | 435/172.3 |
| 5,747,332 | 5/1998 | Wallen et al. | 435/272 |
| 5,830,464 | 11/1998 | Srivastava | 424/93.71 |
| 5,837,251 | 11/1998 | Srivastava | 424/193.1 |
| 5,935,576 | 8/1999 | Srivastava | 424/184.1 |

OTHER PUBLICATIONS

Peng et al., "Purification of immunogenic heat shock protein 70–peptide complexes by ADP–affinity chromatography" in *Journal of Immunological Methods*, 204 (1997) 13–21.
Baltz, "Vaccines in the treatment of Cancer," *Am. J. Health–Syst. Pharm.* (1995), 52:2574–2585.
Blachere et al., "Heat Shock Protein Vaccines Against Cancer," *Journal Of Immunotherapy* (1993), 14:352–356.
Buchner, "Supervising the Fold: Functional Principals of Molecular Chaperones," The FASEB Journal, vol. 10, pp. 10–19, Jan. 1996.
Gao et al., "Effect of Constitutive 70–kDa Heat Shock Protein Polymerization on Its Interaction with Protein Substrate" in *The Journal of Biological Chemistry*, vol. 271 (1996), 28: 16792–16797.
Georgopoulos et al., "Role of the Major Heat Shock Proteins as Molecular Chaperones," Annu. Rev. Cell Biol. 1993, pp. 602–634.
Lefkovits, *Immunological Methods Manual*, vol. 2, Chapter 9.11, (San Diego: Academic Press, 1997).
Li et al., "Tumor rejection antigen gp96/grp94 is an ATPase: implications for protein folding and antigen presentation," *The EMBO Journal*, vol. 12, No. 8 (1993), 3143–3151.
Li et al., "A Critical Contemplation on the Roles of Heat Shock Proteins in Transfer of Antigenic Peptides During Antigen Presentation," *Behring Inst. Mitt.* (1994), 94:37–47.

Moseley, "Mechanisms of heat adaptation: Thermotolerance and acclimization" in *J. Lab. Clin. Med.* (1994), 123:48–52.
Palleros et al., "Interaction of hsp70 with unfolded proteins: Effects of temperatures and nucleotides on the kinetics of binding" in *Proc. Natl. Acad. Sci.* (Jul. 1991), 88:5719–5723.
Palleros et al., "hsp70–Protein Complexes" in *The Journal of Biological Chemistry*, vol. 269 (1994), 18:13107–13114.
Peng et al., "Purification of immunogenic heat shock protein 70–peptide complexes by ADP–affinity chromatography," *Journal of Immunological Methods* (1997) 204: 13–21.
Roman et al., "Synthetic peptides non–covalently bound to bacterial hsp 70 elicit peptide–specific T–cell responses in vivo," *Immunology* (1996) 88: 487–492.
Srivastava, "Peptide–Binding Heat Shock Proteins in the Endoplasmic Reticulum: Role in Immune Response to Cancer and in Antigen Presentation," *Advances in Cancer Research* (1993), 62:153–177.
Srivastava et al., "Heat shock protein–peptide complexes in cancer immunotherapy," *Current Opinion in Immunology* (1994), 6:728–732.
Srivastava et al., "Heat shock proteins transfer peptides during antigen processing and CTL priming," *Immunogenetics* (1994), 39:93–98.
Udono et al., "Heat Shock Protein 70–associated Peptides Elicit Specific Cancer Immunity," *J. Exp. Med.* (1993), 178:1391–1396.
Udono et al., "Comparison of Tumor–Specific Immunogenicities of Stress–Induced Proteins gp96, hsp90, and hsp 70," *Journal of Immunology* (1994), 5398–5403.
Welch et al., "Rapid Purification of Mammalian 70,000–Dalton Stress Proteins: Affinity of the Proteins for Nucleotides," *Molecular and Cellular Biology* (Jun. 1985), 1229–1237.
BIOSIS AN 96;54240, Gao et al., Molecular Biology of the Cell 6 (SUPPL.) (abstract), 1995.

*Primary Examiner*—Dwayne C. Jones
*Assistant Examiner*—C. Delacroix-Muirheid
*Attorney, Agent, or Firm*—Jagtiani & Associates

[57] ABSTRACT

A method for purifying heat shock protein complexes is provided which comprises the steps of adding a solution containing heat shock protein complexes, in which heat shock proteins are associated with peptides, polypeptides, denatured proteins or antigens, to a column containing an ADP matrix to bind the heat shock proteins complexes to the ADP matrix and adding a buffer containing ADP to the column to remove the heat shock protein complexes in an elution product. Additionally a method for synthesizing heat shock protein complexes and purifying the complexes so produced is provided which comprises the steps of adding heat shock proteins to an ADP matrix column to bind them to the matrix, adding a solution of peptides, polypeptides, denatured proteins or antigens to the column to bind them to the heat shock proteins as heat shock protein complexes and adding a buffer containing ADP to the column to remove the complexes in an elution product.

30 Claims, 3 Drawing Sheets

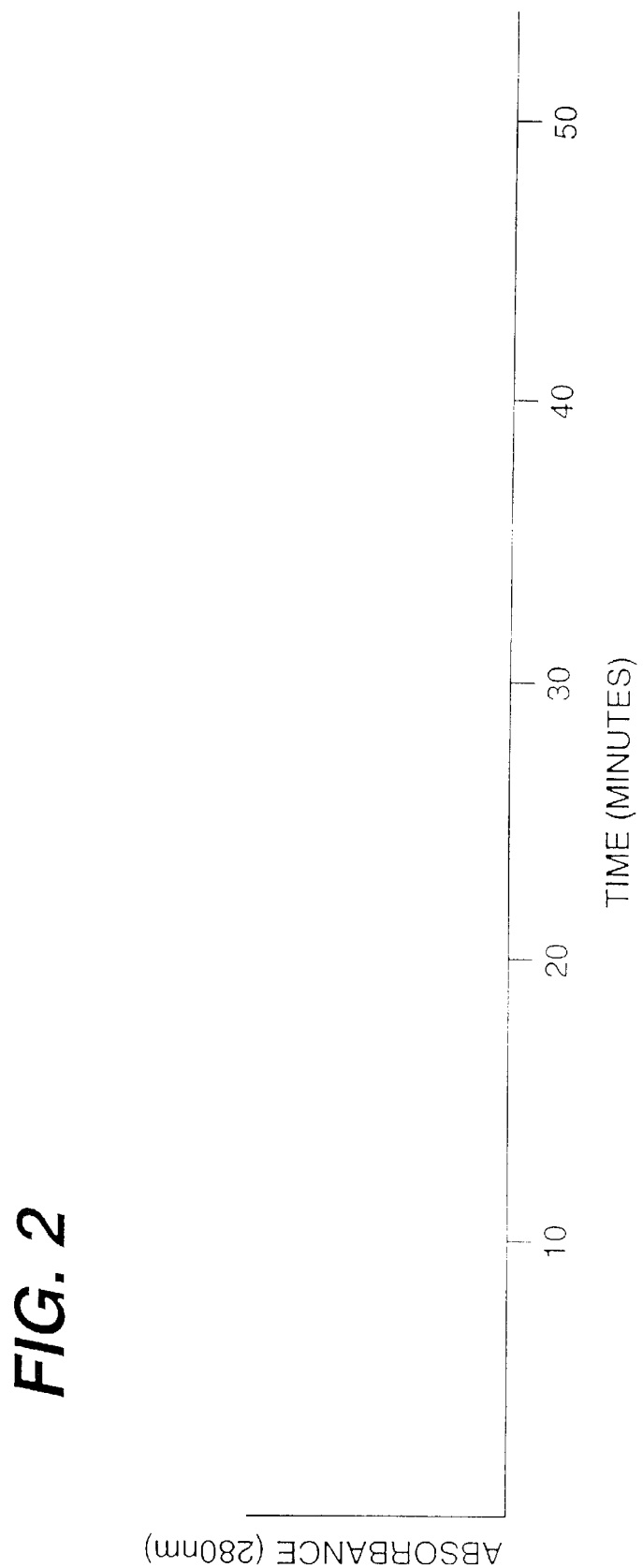

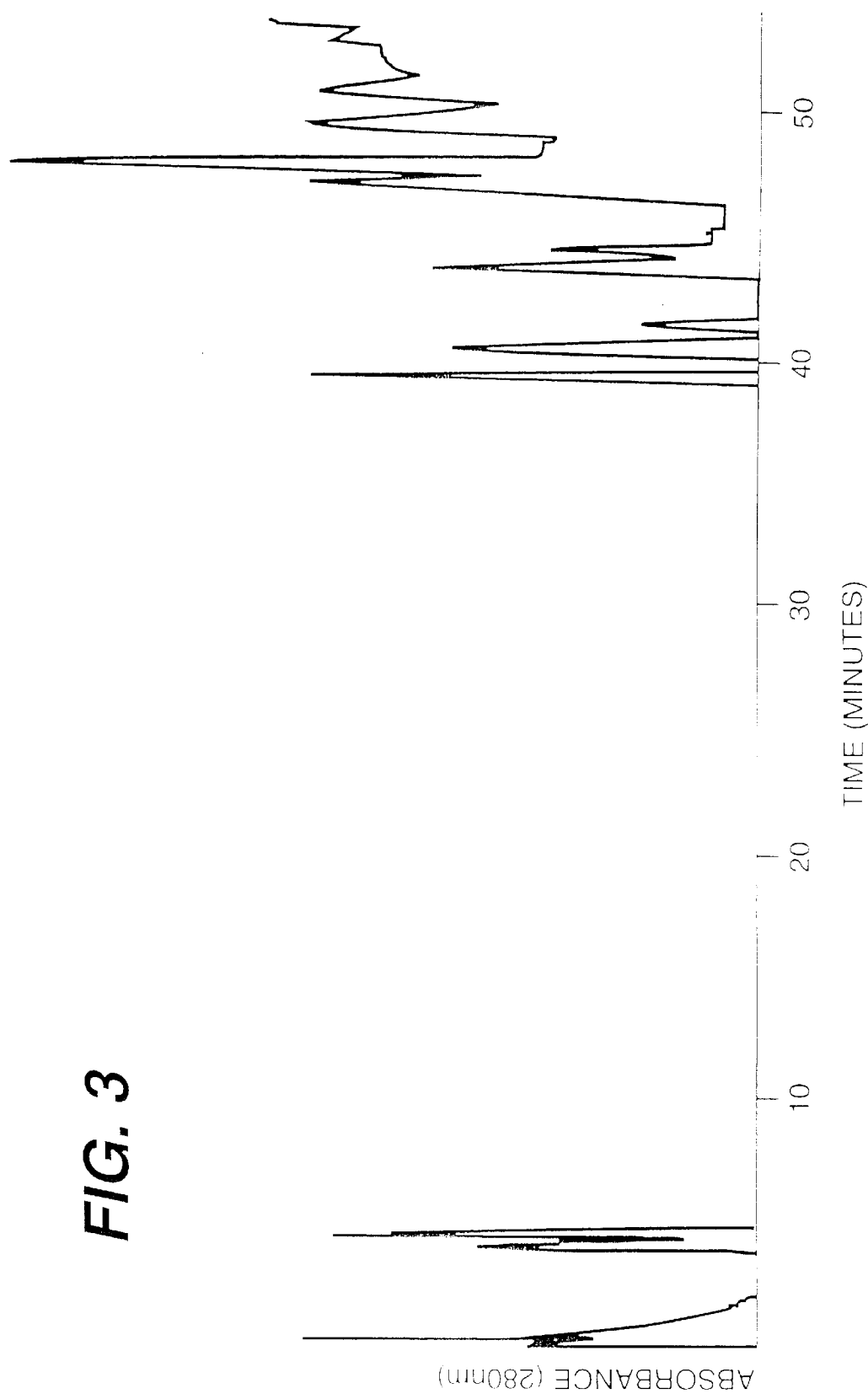

PURIFIED HEAT SHOCK PROTEIN COMPLEXES

This application is a division of application Ser. No. 08/717,239, filed on Sep. 20, 1996, now U.S. Pat. No. 5,747,332.

BACKGROUND OF THE INVENTION

1. Field of the Invention

The present invention relates generally to methods for purifying and synthesizing heat shock protein complexes.

2. Description of the Prior Art

Heat shock proteins (HSPs) are associated in cells with a broad spectrum of peptides, polypeptides, denatured proteins and antigens with which they form complexes. Such HSP-peptide complexes have been described as being useful in vaccines against cancers and infectious diseases by Srivastava et al., "Heat shock protein-peptide complexes in cancer immunotherapy" in *Current Opinion in Immunology* (1994), 6:728–732; Srivastava, "Peptide-Binding Heat Shock Proteins in the Endoplasmic Reticulum" in *Advances in Cancer Research* (1993), 62:153–177. The HSP-peptide complexes appear to work as vaccines, because they may function as antigen carrying and presentation molecules. The development of vaccines using such antigens has been described by Baltz, "Vaccines in the treatment of Cancer" in *Am. J. Health-Syst. Pharm.* (1995), 52:2574–2585. The antigenicity of heat shock proteins appears to derive not from the heat shock protein itself, but from the associated peptides, see Udono et al., "Heat Shock Protein 70-associated Peptides Elicit Specific Cancer Immunity" in *J. Exp. Med.* (1993), 178:1391–1396; Srivastava et al., "Heat shock proteins transfer peptides during antigen processing and CTL priming" in *Immunogenetics* (1994), 39:93–98; Srivastava, "A Critical Contemplation on the Roles of Heat Shock Proteins in Transfer of Antigenic Peptides During Antigen Presentation" in *Behring Inst. Mitt.* (1994), 94:37–47. HSPs appear to be part of the process by which peptides are transported to the Major Histocompatibility Complex (MHC) molecules for surface presentation.

A number of different HSPs have been shown to exhibit immunogenicity including: gp96, hsp90 and hsp70, see Udono et al., supra. and Udono et al., "Comparison of Tumor-Specific Immunogenicities of Stress-Induced Proteins gp96, hsp90, and hsp 70" in *Journal of Immunology* (1994), 5398–5403; gp96 and grp94, Li et al., "Tumor rejection antigen gp96/grp94 is an ATPase: implications for protein folding and antigen presentation" in *The EMBO Journal*, Vol. 12, No. 8 (1993), 3143–3151; and gp96, hsp90 and hsp70, Blachere et al., "Heat Shock Protein Vaccines Against Cancer" in *Journal Of Immunotherapy* (1993), 14:352–356.

Heat shock proteins have been purified using a procedure employing DE52 ion-exchange chromatography followed by affinity chromatography on ATP-agarose, see Welch et al., "Rapid Purification of Mammalian 70,000-Dalton Stress Proteins: Affinity of the Proteins for Nucleotides" in *Molecular and Cellular Biology* (June 1985), 1229–1237. However, previous methods of purifying HSPs such as this one purify the heat shock proteins without the associated peptides. Other methods that do purify HSPs together with their associated peptides are complicated and expensive.

SUMMARY OF THE INVENTION

Therefore, it is an object of the invention to provide a simple and inexpensive method for purifying heat shock proteins together with their associated peptides, polypeptides, denatured proteins or antigens from cell lysates.

It is a further object of the invention to provide a method for synthesizing heat shock protein complexes that is capable of forming these complexes from heat shock proteins and peptides, polypeptides, denatured proteins or antigens from different cells and from different species.

The present invention provides a method for purifying heat shock protein complexes comprising the steps of adding a solution containing heat shock protein complexes, in which heat shock proteins are associated with peptides, polypeptides, denatured proteins or antigens, to a column containing an ADP matrix to bind the heat shock proteins complexes to the ADP matrix and then adding a buffer containing ADP to the column remove the heat shock protein complexes in an elution product.

The present invention also provides a method for synthesizing heat shock protein complexes and purifying the complexes so produced by adding heat shock proteins to an ADP matrix column to bind them to the matrix, adding a solution of peptides, polypeptides, denatured proteins or antigens to the column to bind them to the heat shock proteins as heat shock protein complexes and then adding a buffer containing ADP to the column to remove the complexes in an elution product.

BRIEF DESCRIPTION OF THE DRAWINGS

FIG. 2 is a plot of HPLC data of material treated with NaCl after being purified by the method of the invention and filtered through a 20,000 molecular weight cut-off filter; and FIG. 3 is a plot of HPLC data of material treated with ATP after being purified by the method of the invention and filtered through a 20,000 molecular weight cut-off filter.

DETAILED DESCRIPTION OF THE PREFERRED EMBODIMENT

Figure 1:
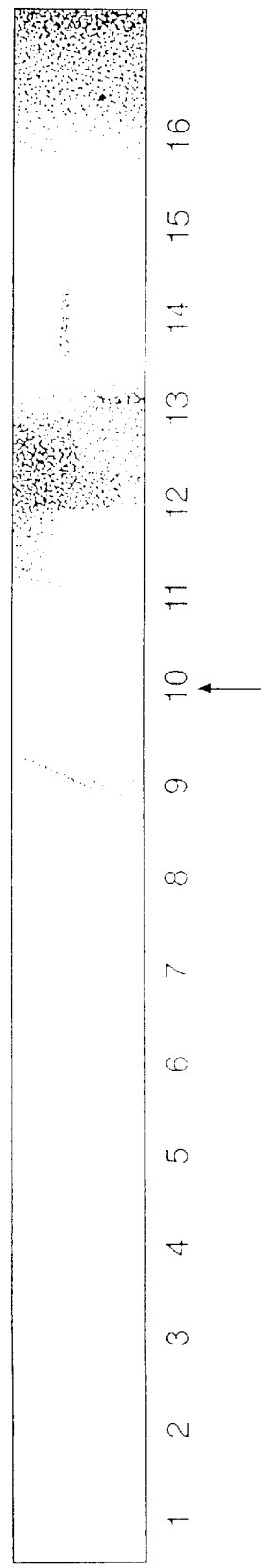
FIG. 1 is a drawing of a western blot of fractions taken from a purification using the ADP purification matrix.

In one preferred embodiment, the present invention provides a method for isolating heat shock protein complexes from a solution containing heat shock proteins using an ADP matrix. Each of the heat shock protein complexes consists of a heat shock protein (HSP) that is bound tightly to an incomplete protein in a cell.

According to the method of the invention, solutions containing these HSP complexes are added to a conventional column, such as an agarose gel column, to which ADP has been added to form an ADP matrix. Suitable ADP-agarose columns include those described in U.S Pat. Nos. 5,114,852; 5,268,465; 5132,407; and 5,541,095, the entire contents and disclosures of which are hereby incorporated by reference. ADP has a strong affinity for the HSP complexes and unlike ATP, does not break down the HSP complexes when it binds to them.

Typically the solution from which the heat shock protein complexes are purified is a cell lysate from a tumor in which the HSPs are already present. However, the invention contemplates that the solution containing HSP complexes to be purified may be produced by mixing an already purified heat shock protein with a cell lysate, a membrane isolate (materials isolated from a cell membrane) or a protease treated cell lysate containing peptides, polypeptides, denatured proteins to produce a solution of HSP complexes. For the purposes of the present invention the term "peptides"

refers to all peptides and polypeptides including denatured proteins, and recombinant or otherwise purified tumor or infectious disease antigens that may be associated with heat shock proteins, either naturally or synthetically.

In order to increase the number of heat shock proteins in the solution added to the ADP matrix column, the solution may be incubated at a temperature of 37 to 50° C. and additional ADP may be added to the solution prior to adding it to the column. If the HSP complex solution is a cell lysate, additional HSPs may be added to the lysate to form additional complexes.

A buffer solution containing ADP is added to the column to elute the HSP complexes from the ADP matrix as an elution product containing the HSP complexes. In addition to ADP, this buffer solution may also contain small amounts of components such as sodium chloride that aid in the removal of the complexes from the ADP matrix.

In order to produce a more purified elution product, after the HSP complexes have been bound to the ADP matrix, a purifying buffer solution may be added to the column to elute other proteins loosely bound to the matrix. This purifying buffer solution preferably contains GTP or another non-adenosine containing nucleotide.

The method of the invention takes advantage of the fact that HSPs are associated with peptides inside the cell. This purification method maintains the HSP-peptide association necessary to develop vaccines or immunotherapeutic tools for tumors and for infectious diseases since HSPs have not been shown to be helpful as antigens without the associated peptides.

In another embodiment the invention provides a method for synthesizing HSP complexes and purifying the complexes so produced. In this method, purified HSPs are bound to an ADP matrix column. Then a preparation of peptides, polypeptides, denatured proteins and/or antigens is added to an ADP matrix column to bind to the HSPs in the matrix. The method then proceeds similarly to the first embodiment of the invention. A buffer solution containing ADP is added to the column to elute the HSP complexes from the ADP matrix as an elution product containing the HSP complexes. This buffer solution may contain small amounts of components such as sodium chloride that aid in the removal of the complexes from the ADP matrix.

As with the first embodiment of the invention, a purifying buffer solution containing GTP or another non-adenosine containing nucleotide may be added to the column to elute other proteins loosely bound to the matrix.

This second embodiment permits HSP complexes to be formed from HSPs and peptides, denatured proteins or antigens from different cells or even different species.

Although there are many heat shock proteins that may be used in the method of the present invention, heat shock proteins that have proven particularly useful include members of the hsp60 family, hsp70 family, hsp90 family and the hsp104–105 family.

Members of the hsp60 family include hsp60, hsp65, rubisco binding protein, and TCP-1 in eukaryotes; and GroEl/GroES in prokaryotes; Mif4, and TCP1alpha and beta in yeast.

Members of the hsp70 family include DnaK proteins from prokaryotes, Ssa, Ssb, and Ssc from yeast, hsp70, Grp75 and Grp78(Bip) from eukaryotes. FIG. 1 is a drawing of a western blot of fractions taken from a purification using the method of the invention. The elution was started at fraction #10 and hsp70 protein appears in fraction #14.

Members of the hsp90 family include hsp90, g96 and grp94.

Members of the hsp104–105 family include hsp105 and hsp110.

The HSP/peptide complexes are eluted from the matrix using an ADP containing buffer. It also helps HSPs to be added to peptide mixtures and the complexes for use as a vaccine.

The invention will now be described by way of example. The following examples are illustrative and are not meant to limit the scope of the invention which is set forth by the appointed claims.

EXAMPLE 1

A confluent T-75 of B16-F1 mouse melanoma cells was rinsed 3× with PBS. 1 ml of PBS was added and the cells were scraped to create a suspension. The suspension was spun for 5 minutes at 1000 rpm to pellet the cells. The supernatant was removed and the cells resuspended in 1.5 ml of a hypotonic buffer (30 mM $NaHCO_3$, pH 7.1). The suspension was transferred to a glass tube and the cells were lysed with a Teflon® pestle and power drill. The lysate was transferred to a microcentrifuge tube and spun at high speed to pellet the undissolved fraction. Total protein of the lysate was determined using the Bradford method. Solution containing 100 μg of total protein was brought up to 300 μl total volume with the addition of Phosphate buffer (0.1M $KH_2PO_4$, 10 mM NaCl, 1 mM EDTA, pH 7.2) and the solution was added to a 5 ml ADP-agarose column (linked through C-8, Sigma Chemical Co.) and allowed to run into the column with 5 ml of Phosphate buffer and then buffer B (20 mM TRIS, 20 mM NaCl, 15 mM EDTA, 15 mM Beta-mercaptoethanol, pH 7.5) with 60 mM ADP was added at the start of fraction 10 to elute the complexes. After completion of the run, 50 μl of each fraction was run onto a 7.5% SDS PAGE gel, transferred to nitrocellulose, probed with an antibody for the inducible and constitutive hsp70 (N27, Stressgen Biotechnologies), and then a secondary alkaline phosphate linked antibody. A blot was developed in a buffer containing BCIP and NBT. A drawing of this plot is shown in FIG. 1.

EXAMPLE 2

PC-3 lysate was run over a agarose column containing an ADP matrix according the method of the invention. The HSP containing fraction was then eluted with ADP. The eluted fraction containing HSPs was filtered using a 20,000 molecular weight cut-off (MWC) filter and several rinses of buffer A (25 mMTris, 20 mM Hepes, 47.5 mM KCl, and 2.25 mM Mg(OAc)2, pH 7.2) were applied. The sample was split into two microcentrifuge tubes and either ATP (to 10 mM) or NaCl (to 1 mM) was added. The tubes were then incubated overnight at 37° C. Each solution was then spun through a 20,000 MWC filter and the filtered material was applied to an HPLC column. The HPLC was accomplished using a C18 reverse phase column (Vydac, 201TB54). The starting buffer was 0.1% TFA in $dH_2O$ and the material was eluted using a gradient of 0.1% TFA in ACN. FIG. 2 shows HPLC data for the material treated with NaCl after being purified with the ADP matrix and filtered through the 20,000 molecular weight cut-off filter. FIG. 3 shows the HPLC data for the material treated with ATP after being purified with the ADP matrix and filtered through the 20,000 molecular weight cut-off filter. The HPLC data in FIGS. 2 and 3 is consistent with the data for hsp70 described in Udono et al., "Heat Shock Protein 70-associated Peptides Elicit Specific Cancer Immunity" in *J. Exp. Med.* (1993), 178:1391–1396.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed:

1. A purified ADP-heat shock protein-peptide complex, wherein said heat shock protein is selected from the group consisting of hsp60, hsp65, rubisco binding protein and TCP-1 from eukaryotes; GroEL/GroES, Mif4, TCPalpha and TCPbeta from yeast.

2. The purified ADP-heat shock protein-peptide complex of claim 1, wherein a heat shock protein-peptide portion of said ADP-heat shock protein-peptide complex comprises a non-naturally occurring heat shock protein-peptide combination.

3. The ADP-heat shock protein-peptide complex of claim 2, wherein said heat shock protein-peptide portion of said complex comprises a heat shock protein from one cell and a peptide from a second cell of the same individual.

4. The ADP-heat shock protein-peptide complex of claim 2, wherein said heat shock protein-peptide portion of said complex comprises a heat shock protein from one individual and a peptide from a second individual.

5. The ADP-heat shock protein-peptide complex of claim 2, wherein said heat shock protein-peptide portion of said complex comprises a heat shock protein from one organism and a peptide from a second organism.

6. The ADP-heat shock protein-peptide complex of claim 2, wherein said heat shock protein-peptide portion of said complex comprises a heat shock protein from one species and a peptide from a second species.

7. A purified ADP-heat shock protein-peptide complex, wherein said heat shock protein is selected from the group consisting of hsp104, hsp105 and hsp110.

8. The purified ADP-heat shock protein-peptide complex of claim 7, wherein a heat shock protein-peptide portion of said ADP-heat shock protein-peptide complex comprises a non-naturally occurring heat shock protein-peptide combination.

9. The ADP-heat shock protein-peptide complex of claim 8, wherein said heat shock protein-peptide portion of said complex comprises a heat shock protein from one cell and a peptide from a second cell of the same individual.

10. The ADP-heat shock protein-peptide complex of claim 8, wherein said heat shock protein-peptide portion of said complex comprises a heat shock protein from one individual and a peptide from a second individual.

11. The ADP-heat shock protein-peptide complex of claim 8, wherein said heat shock protein-peptide portion of said complex comprises a heat shock protein from one organism and a peptide from a second organism.

12. The ADP-heat shock protein-peptide complex of claim 8, wherein said heat shock protein-peptide portion of said complex comprises a heat shock protein from one species and a peptide from a second species.

13. A purified ADP-heat shock protein-peptide complex, wherein said heat shock protein is selected from the group consisting of DnaK proteins from prokaryotes.

14. The purified ADP-heat shock protein-peptide complex of claim 13, wherein a heat shock protein-peptide portion of said ADP-heat shock protein-peptide complex comprises a non-naturally occurring heat shock protein-peptide combination.

15. The ADP-heat shock protein-peptide complex of claim 14, wherein said heat shock protein-peptide portion of said complex comprises a heat shock protein from one cell and a peptide from a second cell of the same individual.

16. The ADP-heat shock protein-peptide complex of claim 14, wherein said heat shock protein-peptide portion of said complex comprises a heat shock protein from one individual and a peptide from a second individual.

17. The ADP-heat shock protein-peptide complex of claim 14, wherein said heat shock protein-peptide portion of said complex comprises a heat shock protein from one organism and a peptide from a second organism.

18. The ADP-heat shock protein-peptide complex of claim 14, wherein said heat shock protein-peptide portion of said complex comprises a heat shock protein from one species and a peptide from a second species.

19. A purified ADP-heat shock protein-peptide complex, wherein said heat shock protein is selected from the group consisting of Ssa, Ssb, and Ssc from yeast.

20. The purified ADP-heat shock protein-peptide complex of claim 19, wherein a heat shock protein-peptide portion of said ADP-heat shock protein-peptide complex comprises a non-naturally occurring heat shock protein-peptide combination.

21. The ADP-heat shock protein-peptide complex of claim 20, wherein said heat shock protein-peptide portion of said complex comprises a heat shock protein from one cell and a peptide from a second cell of the same individual.

22. The ADP-heat shock protein-peptide complex of claim 20, wherein said heat shock protein-peptide portion of said complex comprises a heat shock protein from one individual and a peptide from a second individual.

23. The ADP-heat shock protein-peptide complex of claim 20, wherein said heat shock protein-peptide portion of said complex comprises a heat shock protein from one organism and a peptide from a second organism.

24. The ADP-heat shock protein-peptide complex of claim 20, wherein said heat shock protein-peptide portion of said complex comprises a heat shock protein from one species and a peptide from a second species.

25. A purified ADP-heat shock protein-peptide complex, wherein said heat shock protein is selected from the group consisting of Grp75 and Grp78(Bip) from eukaryotes.

26. The purified ADP-heat shock protein-peptide complex of claim 25, wherein a heat shock protein-peptide portion of said ADP-heat shock protein-peptide complex comprises a non-naturally occurring heat shock protein-peptide combination.

27. The ADP-heat shock protein-peptide complex of claim 26, wherein said heat shock protein-peptide portion of said complex comprises a heat shock protein from one cell and a peptide from a second cell of the same individual.

28. The ADP-heat shock protein-peptide complex of claim 26, wherein said heat shock protein-peptide portion of said complex comprises a heat shock protein from one individual and a peptide from a second individual.

29. The ADP-heat shock protein-peptide complex of claim 26, wherein said heat shock protein-peptide portion of said complex comprises a heat shock protein from one organism and a peptide from a second organism.

30. The ADP-heat shock protein-peptide complex of claim 26, wherein said heat shock protein-peptide portion of said complex comprises a heat shock protein from one species and a peptide from a second species.

* * * * *